(12) United States Patent
Mills et al.

(10) Patent No.: US 6,561,994 B1
(45) Date of Patent: *May 13, 2003

(54) WRIST BRACE

(75) Inventors: Jessica A. Mills, Mason, OH (US); Richard G. Taylor, Cincinnati, OH (US); Ralph M. Buschbacher, Carmel, IN (US)

(73) Assignee: Beiersdorf Inc., Wilton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/062,148

(22) Filed: Jan. 31, 2002

(51) Int. Cl.[7] .................................................. A61F 5/00
(52) U.S. Cl. ......................................... 602/20; 602/21
(58) Field of Search ....................... 602/20, 21, 60–64; 128/877–878; 2/16, 18, 20, 161.1, 162, 910

(56) References Cited

U.S. PATENT DOCUMENTS

| | | | | |
|---|---|---|---|---|
| 5,092,318 A | * | 3/1992 | More .......................... | 602/27 |
| 5,421,811 A | * | 6/1995 | More .......................... | 602/21 |
| 5,759,166 A | * | 6/1998 | Nelson ........................ | 602/21 |
| 6,024,715 A | * | 2/2000 | Maxwell ...................... | 602/64 |
| 6,186,969 B1 | * | 2/2001 | Bell ........................ | 602/64 XZ |

* cited by examiner

*Primary Examiner*—Michael A. Brown
(74) *Attorney, Agent, or Firm*—Alston & Bird LLP

(57) ABSTRACT

Wrist brace including a sheet of flexible material having a first portion of which is formed of a substantially non-stretchable material and a second portion of which is formed of a stretchable material, said first and second portions being joined along a junction extending from the distal edge of said sheet to the proximal edge of said sheet, said junction being closer to one later al edge at the distal end and further away from said lateral edge at the proximal end.

7 Claims, 5 Drawing Sheets

WRIST BRACE

BACKGROUND OF THE INVENTION

This invention relates to orthopedic wrist braces, more particularly, to a novel wrist brace which combines elastic and nonelastic fabric in its construction. The novel wrist brace makes it possible to vary the compression on the proximal portion of the wrist which is sought to be immobilized, while at the same time retaining freedom of movement of the distal portion of the hand.

A wide variety of wrist support devices are known in the art. These include various types of sleeves and wraps, some of which are adjustable and some of which are not.

A recent improvement in the state of the art is disclosed in U.S. Pat. No. 5,728,059, which discloses a wrist support comprised of a sheet of flexible elastic material having pockets for a rigid splint. The splint is formed with a curvature to conform to the user's wrist and palm. With the splint inserted into one of the pockets, the wrist support is wrapped around the wrist and hand and secured in place with a plurality of fastening wraps. The compression applied to the wrist by the wrist brace is adjustable by the fastening wraps, the position of which effects the degree of stretch of the elastic fabric, and thereby the compression on the wrist and hand.

U.S. Pat. No. 5,769,804 describes a wrist brace which comprises a preformed shell, with an elastic tongue which extends across the shell (after the manner of a tongue in a shoe). The patient's hand is inserted into and through the shell, after which the shell is tightened using a multi-string lace extending over the elastic tongue. The device is said to provide even distribution of all forces to immobilize the wrist, but, having a shell composed of a three-layer composite including a thermoformable plastic, would appear to be relatively inflexible. In addition, the need to apply tension to the laces at the same time the fastening straps to which said laces are attached are latched makes this device relatively complicated to use.

The prior art devices generally apply uniform compression over and around all portions of the wrist and hand to which they are applied. It would, however, be desirable to be able to apply greater compression to the proximal wrist, where it is needed, while at the same time maintaining a lesser compression on those portions of the hand where such compression is not needed and increased flexibility is desired.

It is therefore an object of the present invention to provide a wrist brace which enables the amount of compression applied to the regions of the hand and wrist to be different, so that a higher compression can be applied to the proximal wrist area while a lesser compression is applied to the distal hand region.

It is a further object of the invention to provide a wrist brace which is easily applied and adjusted.

It is still a further object of the present invention to provide an elastic wrist brace which avoids the use of natural latex.

SUMMARY OF THE INVENTION

These and other objects are achieved by the wrist brace of the present invention, which comprises a sheet of flexible material having an inner surface and an outer surface, a distal edge, proximal edge and opposite first and second lateral edges; the first of said lateral edges being provided with a plurality of fastening straps extending laterally, and being fastenable to a outer surface of said sheet of flexible material, a first portion of said sheet being formed of a substantially non-stretchable material and a second portion of which is formed of a stretchable material, said first and second portions being joined along a junction extending from the distal edge of said sheet to the proximal edge of said sheet, said junction being closer to the second of said lateral edges at the distal edge and spaced further apart from said second lateral edge at the proximal edge of said sheet.

In a preferred embodiment, the wrist brace of the present invention further comprises a pocket, running longitudinally between the proximal edge and the distal edge, secured on the outside surface of the sheet, such as by sewing, and having an inward kink at the distal end thereof. The pocket is adapted to accommodate a substantially inflexible splint, which itself is adapted to the anatomy of the inner surface of a human hand. The splint may be made of, for example, aluminum or plastic.

It is also preferred that the fastening straps and the outer surface of the sheet material be provided with complementary hook and loop fastening means, such as that sold under the trademark VELCRO®, although other fastening means, such as buckles, snap-on connectors and the like could also be used.

In a further preferred embodiment, at least one of the fastening straps is of a length sufficient to wrap completely around the wrist of a patient when the wrist brace is applied to the patient's wrist.

In a particularly preferred embodiment, the wrist brace includes a substantially inflexible splint inserted in the longitudinal pocket, said splint having a curvature at its distal end to fit the concave palmer area above the lunate bone.

Optionally, the splint is reversible to fit either the left hand or the right hand.

These and other aspects, features and advantages of the present invention will become apparent from the following detailed description taken in conjunction with the accompanying drawings.

DETAILED DESCRIPTION

Figure 1:
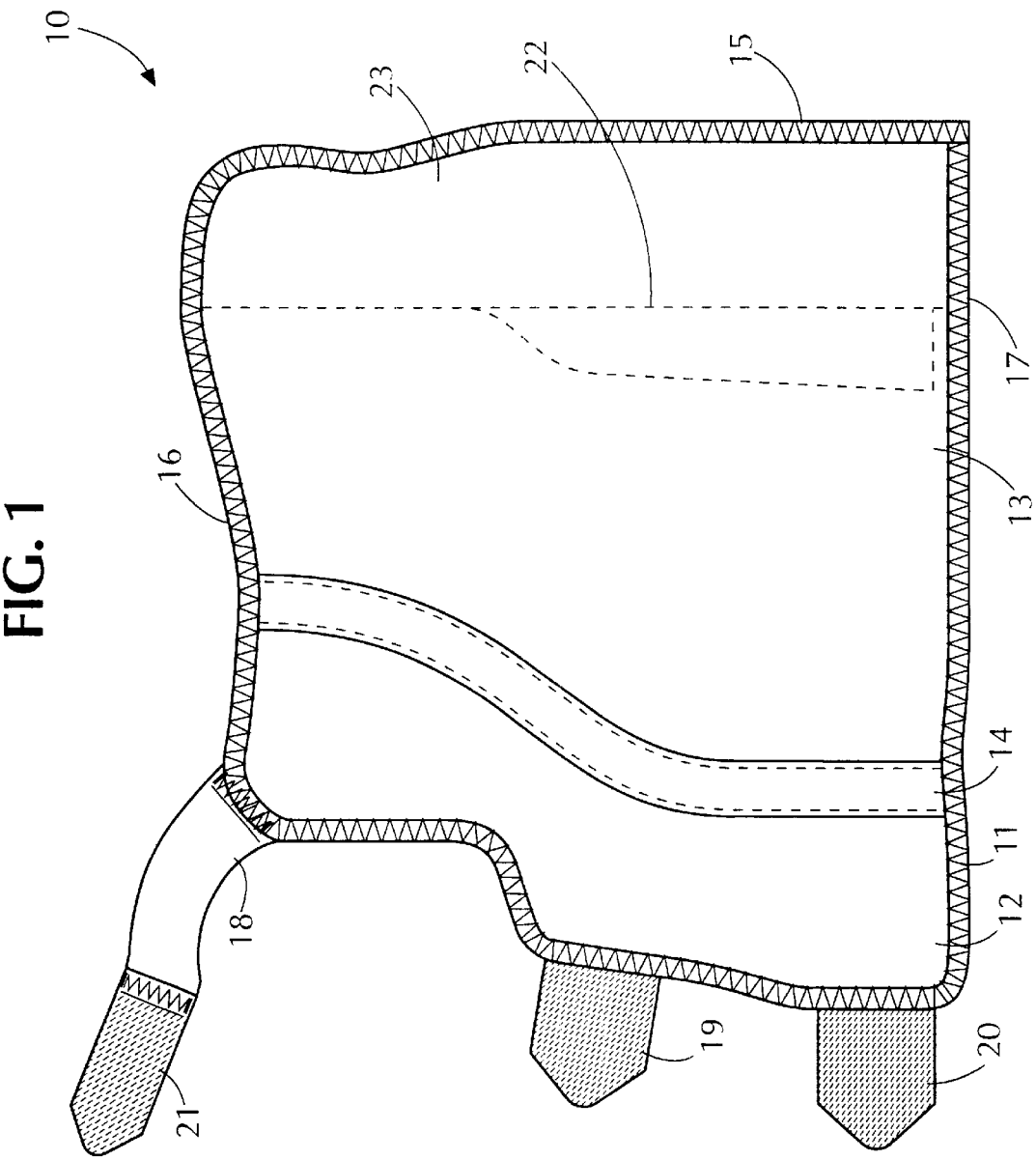
FIG. 1 is a top view of the inside surface of the wrist brace of the present invention.

The wrist brace 10, shown in FIG. 1, is formed of a sheet 11 of flexible material having a stretchable portion 12 and a non-stretchable portion 13 joined to each other along a generally spiraled junction 14. The spiraled junction is closer to lateral edge 15 at distal edge 16 than it is to lateral edge 15 at proximal edge 17. The width of the non-stretchable portion 13 of sheet 11 is thus greater at the proximal end and narrower at the distal end of the sheet.

Also shown in FIG. 1 are fastening straps 18, 19 and 20 having one portion 21, 22, 23 of complementary hook and loop fasteners, said portion being either the hook portion or the loop portion.

Figure 2:
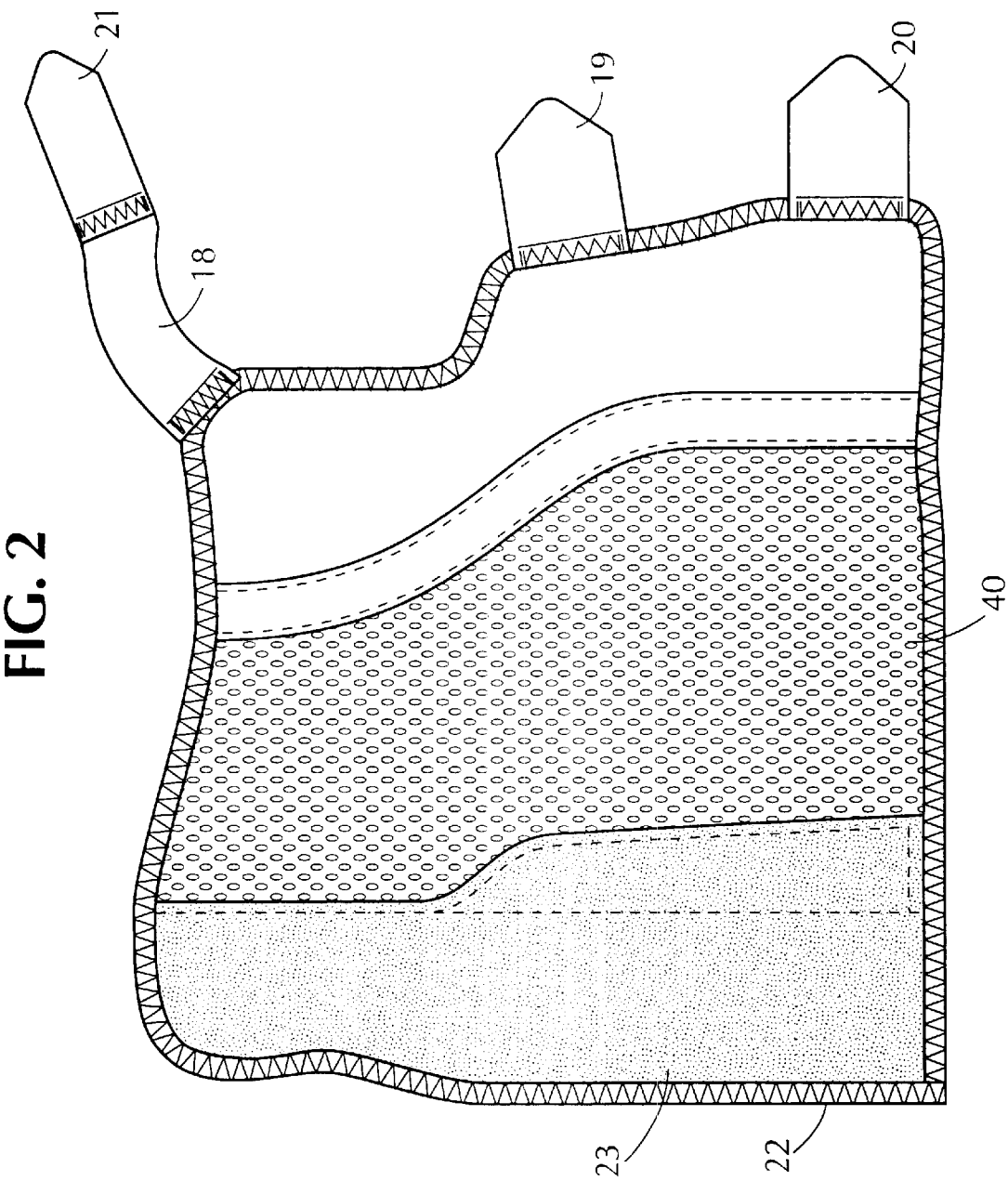
FIG. 2 is a top view of the outside surface of the wrist brace of the present invention.

FIG. 2 shows the outer side of the wrist brace shown in FIG. 1, wherein fastening straps 18 and 19 are formed from either the hook or loop portion of a hook and loop fastening system, and strap 18 is formed of a stretchable or non-stretchable material to which either the hook or loop portion 21 of a hook and loop fastening system is attached. Also shown in FIG. 2 is longitudinal pocket 22 into which a splint, as shown in. FIGS. 5–8, may be inserted.

The exposed surface of pocket 22 is provided with a portion of hook and loop fastening material 23 that complements the portion of hook and loop material 19, 20, 21 so that the hook or loop material of the straps is attachable to the surface of pocket 22 by said hook and loop means. The hook and loop fastening portion 23 may, alternatively, be located at another position on the outside surface of wrist brace 10 instead of or in addition to the location on the exposed surface of pocket 22.

Figure 3:
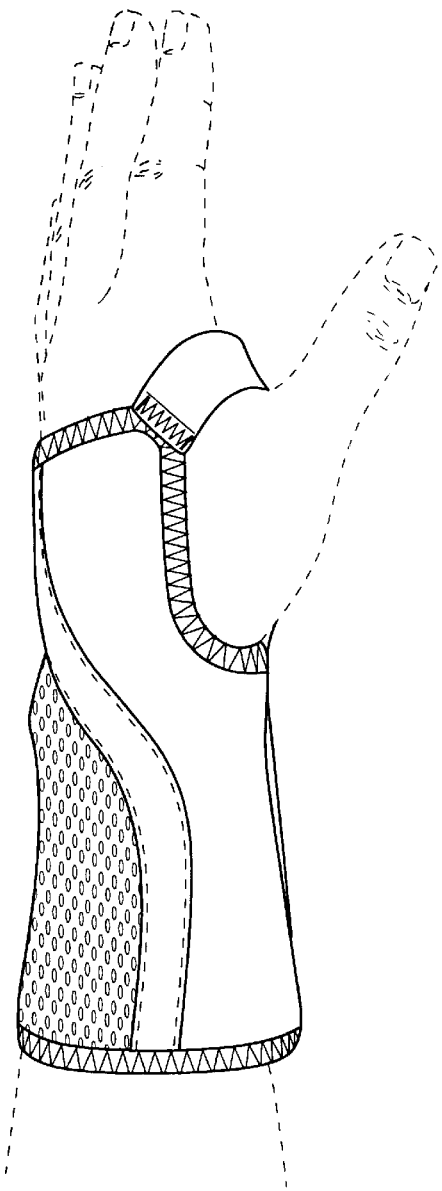
FIG. 3 is a view of the wrist brace as applied to a human hand.

FIG. 3 depicts the wrist brace as applied to a human hand.

Figure 4:
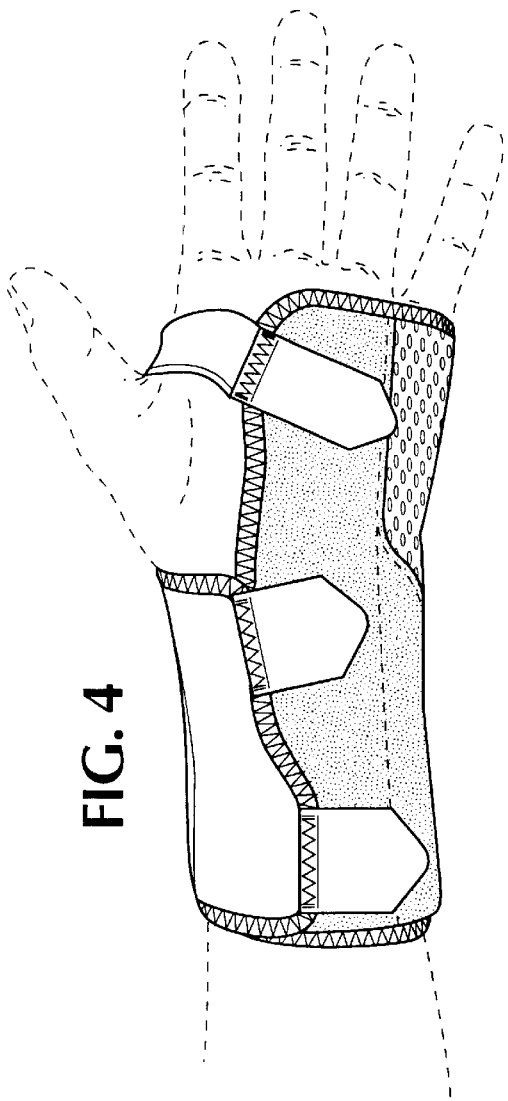
FIG. 4 depicts the wrist brace of FIG. 3, viewed from the palmer side.

FIG. 4 depicts the palmer side of the wrist brace as applied to the human hand.

In a particularly preferred embodiment, at least one of the fastening straps, preferably middle strap 19, is constructed of a length sufficient to wrap completely around the wrist.

Figure 8:
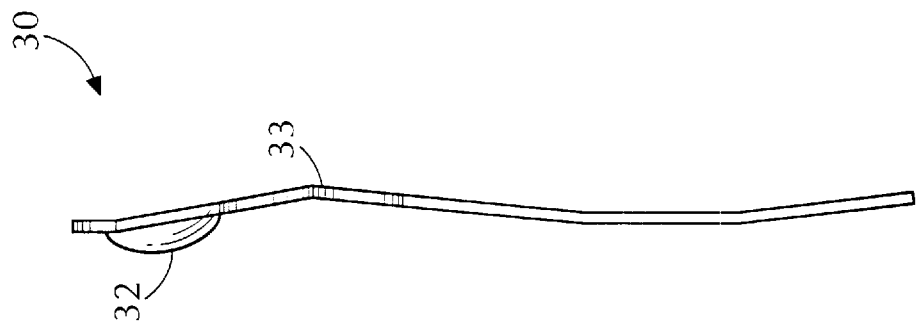
FIG. 8 is a side view of the splint of FIGS. 7, 9 & 10, having a bend
Figure 7:
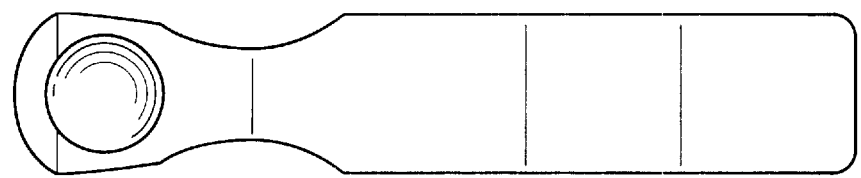
FIG. 7 is a front view of an alternative embodiment of the splint of FIG. 5.
Figure 6:
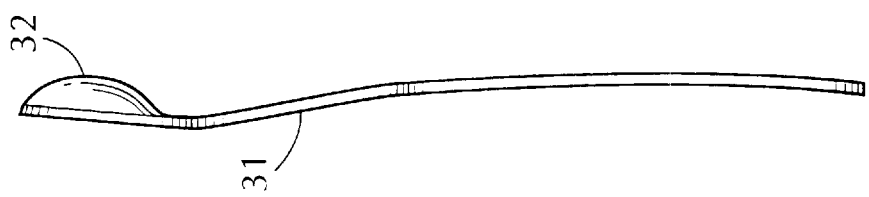
FIG. 6 is a side view of the splint of FIG. 5, having a curvature.
Figure 5:
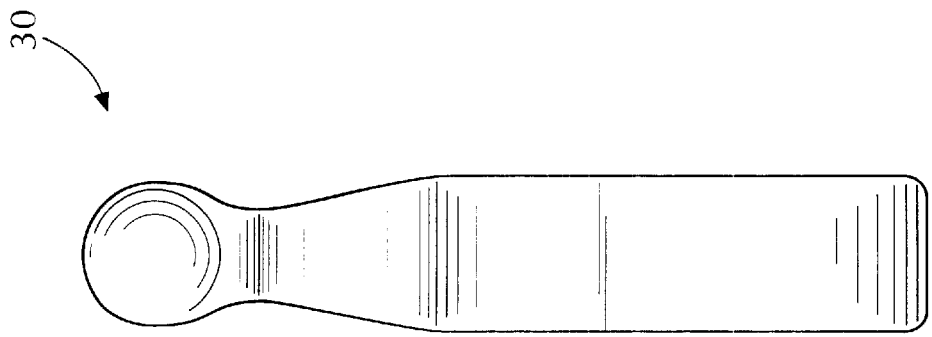
FIG. 5 is a front view of a splint used with a wrist brace for either the right or left hands.
Figure 10:
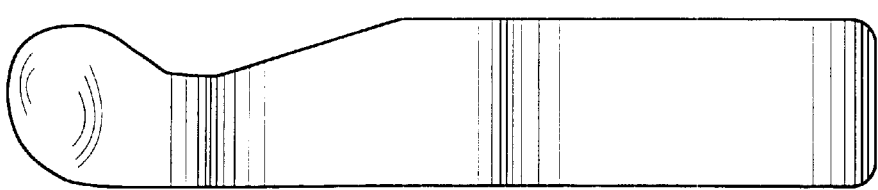
FIG. 10 is a front view of an alternative splint, used with a wrist brace for the left hand.
Figure 9:
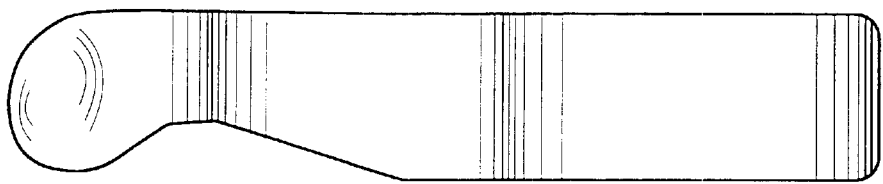
FIG. 9 is a front view of an alternative splint, used with a wrist brace for the right hand.

FIGS. 5–10 illustrate the splint 30 which can be inserted into pocket 22 of the wrist support. FIG. 5 illustrates a frontal view of a splint which can be used with a wrist brace for the right or left hands, and FIG. 6 illustrates a side view of the splint of FIG. 5, showing the curvature 31. FIG. 7 illustrates an alternative embodiment of the splint of FIG. 5. FIG. 8 illustrates a side view of the splint of FIGS. 7, 9 & 10, showing the bend 33. FIG. 9 illustrates a frontal view of a splint for use in a wrist brace for the right hand, and FIG. 10 illustrates a splint for use in a wrist brace for the left hand.

The splint 30 is an elongated member, preferably of a thin, rigid material such as metal or plastic. The splint material may also be chosen to provide some flexibility to permit limited flexion and extension movement of the user's wrist. The longitudinal and lateral dimensions of the splint are selected so that it fits in the pocket 22 to extend substantially from the proximal end to the distal end of the wrist support 10. The splint 30 is shaped with a curvature 31, as shown in the side view of FIG. 6, or a bend 33, as shown in FIG. 8, to conform to the palm and wrist of the user to maintain the hand slightly in extension relative to the wrist.

The splint optionally further includes a convex surface 32, to conform with the palmar cavity of the user's hand.

The convex surface 32 may be formed by simply pressing one side of the splint to produce a concave hollow therein, thereby forming a complementary convex surface on the opposite side.

The non-stretch portion 13 of wrist brace 10 may be constructed of any fabric that is non-stretchable or substantially non-stretchable. Preferably, the material will be one that contains no natural latex, since in some cases, natural latex products can cause allergic reactions to skin that is in contact with it. The non-stretch material should also be comfortable to the skin, and breathable, so that moisture can pass through it from the skin to the atmosphere. The material is preferably dimensionally stable. There are a wide variety of materials that will meet these criteria, such as the material marketed by GEHRING TEXTILES, INC.® as SPACER FABRICS, and those marketed by GUILFORD HILLS, INC. as COOL FLEX™ fabric. A further example of fabric that can be used as the non-stretch portion of wrist brace 10 is that disclosed in U.S. Pat. No. 5,385,036.

The breathability of the fabric may optionally be enhanced by providing openings or holes 40 in or through it, as illustrated in FIG. 2.

The stretch portion of wrist brace 10 can be constructed of any of a variety of flexible and elastic materials. Such materials may be of the type that is elastic in one direction only, in which case stretch portion 12 of wrist brace 10 will be elastic in the lateral (i.e., lateral edge to lateral edge) direction only; or the materials may be elastic in both the lateral and longitudinal (i.e., distal edge to proximal edge) directions. The stretch portion of wrist brace 10 preferably contains no natural latex or natural latex products. Representative materials usable for this purpose are any material possessing elastic properties; for example, woven, non-woven or knit elastics, neoprene, neoprene blends, foams or laminates.

The foregoing has described the preferred principles, embodiments and modes of operation of the present invention; however, the invention should not be construed as limited to the particular embodiments discussed. Instead, the above-described embodiments should be regarded as illustrative rather than restrictive, and it should be appreciated that variations, changes and equivalents may be made by others without departing from the scope of the present invention as defined by the following claims.

We claim:

1. A wrist brace comprising a sheet of flexible material having an inner surface, an outer surface, a distal edge, proximal edge and opposite lateral edges; a first of said lateral edges being substantially straight and a second lateral edge being provided with a plurality of fastening straps extending laterally, and being fastenable to the outer surface of said sheet of flexible material, a first portion of said sheet being formed of a substantially non-stretchable material and a second portion of which is formed of a stretchable material, said first and second portions being joined along a junction extending from the distal edge of said sheet to the proximal edge of said sheet, said junction being closer to said first lateral edge at the distal edge and spaced further apart from said first lateral edge at the proximal edge of said sheet.

2. The wrist brace of claim 1, wherein said junction is a generally spiraled junction.

3. The wrist brace of claim 1, further comprising a pocket, running longitudinally between the proximal edge and the distal edge of said sheet, secured on the outside surface of said sheet and adapted to accommodate a substantially inflexible splint.

4. The wrist brace of claim 3, further comprising a substantially inflexible splint, inserted in said pocket.

5. The wrist brace of claim 4, wherein said splint has a curvature adapted to fit the concave palmar area above the lunate bone, and is reversible to fit either the left hand or the right hand.

6. The wrist brace of claim 1, wherein said fastening straps and the outside surface of said sheet are provided with complementary hook and loop fastening elements of a hook and loop fastening system.

7. The wrist brace of claim 1, wherein at least one of said fastening straps is of a length sufficient to wrap completely around the wrist of a patient when the wrist brace is applied to the patient's wrist.

* * * * *